United States Patent
Kim et al.

(10) Patent No.: US 7,608,741 B2
(45) Date of Patent: Oct. 27, 2009

(54) **MASS SEPARATION METHOD OF MAGNOLOL FROM *MAGNOLIAE* CORTEX RADIX**

(75) Inventors: Jin Sook Kim, Seoul (KR); Yun Mi Lee, Gyeonggi-do (KR); Dae Sik Jang, Seoul (KR)

(73) Assignee: Korea Institute of Oriental Medicine, Daejeon (KR)

( * ) Notice: Subject to any disclaimer, the term of this patent is extended or adjusted under 35 U.S.C. 154(b) by 0 days.

(21) Appl. No.: 11/915,721

(22) PCT Filed: Jun. 21, 2005

(86) PCT No.: PCT/KR2005/001914
§ 371 (c)(1), (2), (4) Date: Nov. 27, 2007

(87) PCT Pub. No.: WO2006/129898
PCT Pub. Date: Dec. 7, 2006

(65) Prior Publication Data
US 2008/0188693 A1  Aug. 7, 2008

(30) Foreign Application Priority Data
May 30, 2005  (KR) ............ 10-2005-0045696

(51) Int. Cl.
*C07C 39/12* (2006.01)
(52) U.S. Cl. .................................. 568/730
(58) Field of Classification Search ........... 568/730
See application file for complete search history.

(56) References Cited

U.S. PATENT DOCUMENTS 5,053,548 A * 10/1991 Tanaka et al. ............. 568/47

FOREIGN PATENT DOCUMENTS

CN    2003-10121303    * 12/2003

\* cited by examiner

*Primary Examiner*—Karl J Puttlitz
(74) *Attorney, Agent, or Firm*—Birch, Stewart, Kolasch & Birch, LLP

(57) ABSTRACT

The present invention related to method for the mass separation of magnolol from Magnoliae cortex or Magnoliae radix. The method comprises the steps of: 1) crushing Magnoliae cortex or Magnoliae radix, extracting the crushed material with organic solvent, adding n-hexane to the extract so as to obtain a n-hexane layer; 2) concentrating the n-hexane layer in a water bath at a temperature of 30-40° C. and a revolution speed of 40-200 RPM under reduced pressure so as to form a crude crystal; and 3) removing the n-hexane from the crude crystal, completely dissolving the crude crystal in chloroform, adding n-hexane to the n-hexane-containing solution, and leaving the solution to stand at room temperature so as to recrystallize the solution. In the method, a column chromatography step which is necessarily carried out in the general separation process is omitted so that separation process steps are reduced, leading to a saving in separation time. Also, expensive equipment is not required, leading a reduction in separation cost. Accordingly, the method is effective for the mass separation of expensive magnolol.

6 Claims, 2 Drawing Sheets

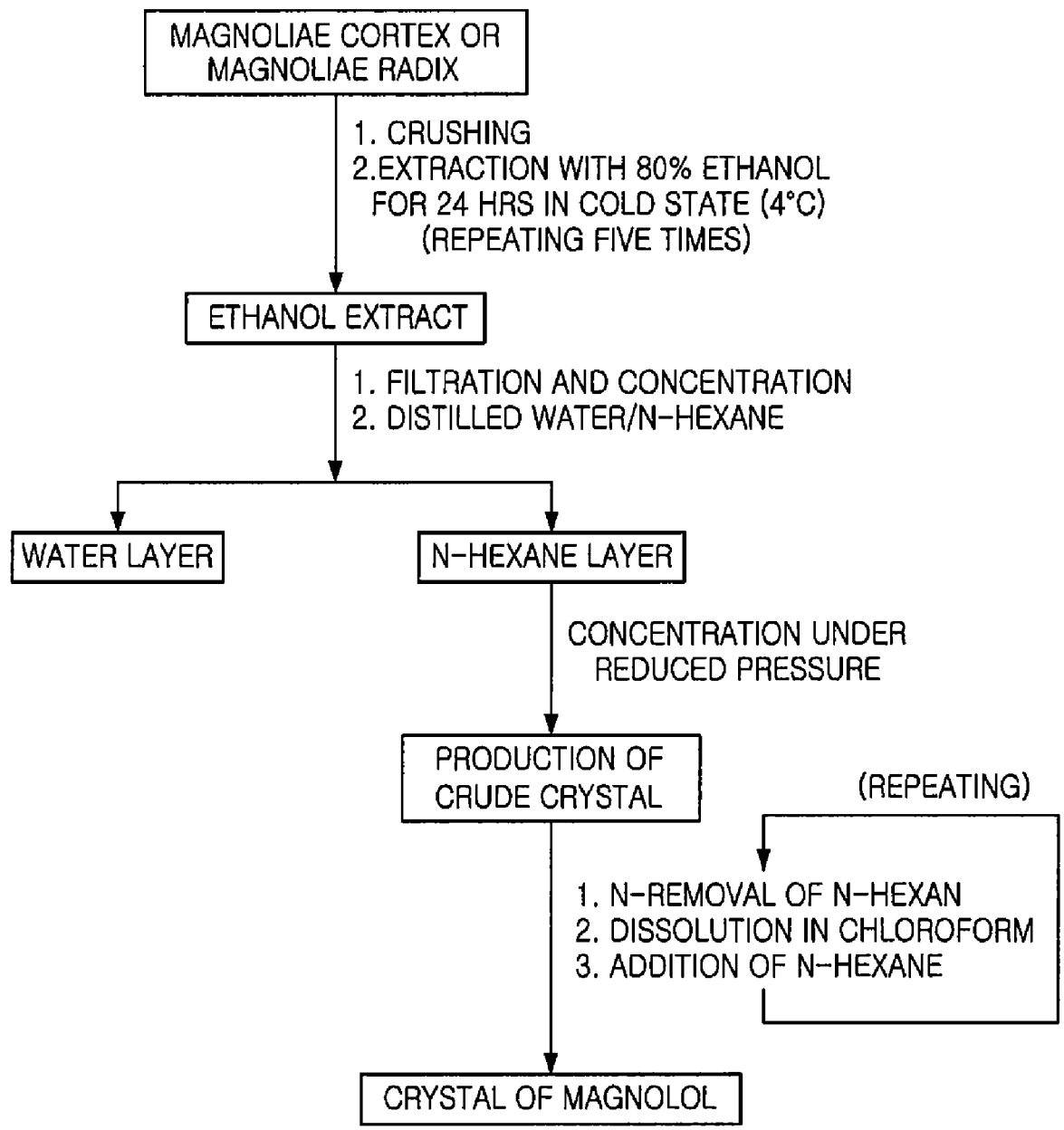
[Fig. 1]

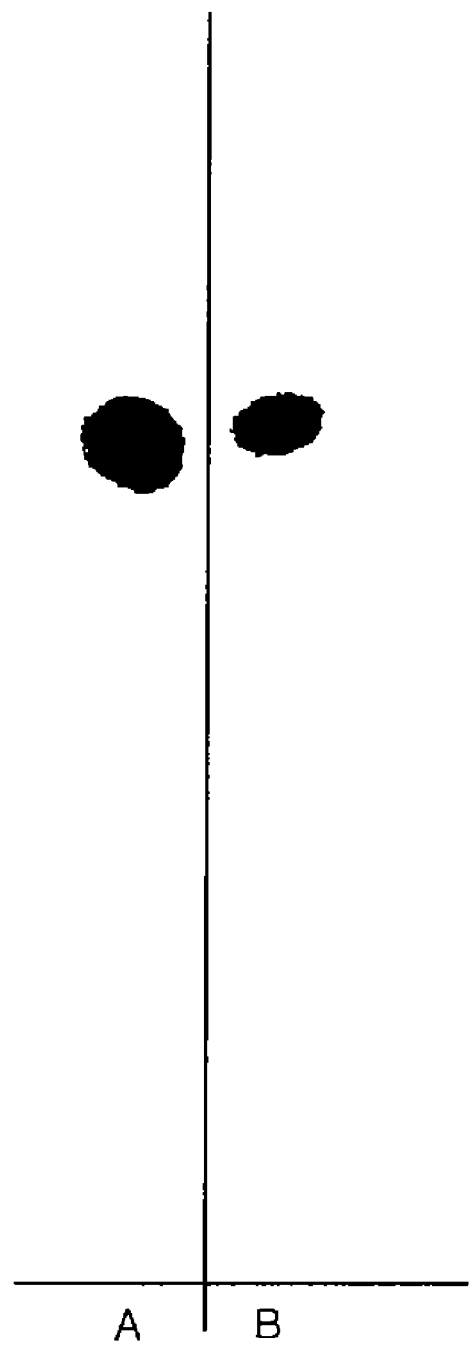
[Fig. 2]
TLC CONDITIONS
STATIONARY PHASE: NORMAL SILICA GEL
MOBILE PHASE : N-HEXANE/EtOAc = 1:1
A : CRYSTAL (MAGNOLOL) BEFORE
    RE-CRYSTALLIZATION
B : CRYSTAL (MAGNOLOL) AFTER
    RE-CRYSTALLIZATION

MASS SEPARATION METHOD OF MAGNOLOL FROM *MAGNOLIAE* CORTEX RADIX

TECHNICAL FIELD

The present invention relates to a method for the mass separation of magnolol from Magnoliae cortex or Magnoliae radix, which allows magnolol to be separated from Magnoliae cortex or Magnoliae radix in large amounts by a simple separation process at low cost.

BACKGROUND ART

Magnoliae cortex and Magnoliae radix, which are the dried cortex and radix of perennial plant *Magnolia officinalis* REHD. et WILS and relatives belonging to Magnoliaceae, are known to have the effects of eliminating dampness and phlegm and promoting the circulation of "Gi", and thus, treating the following symptoms: retention of dampness and acupuncture of the diaphragm; numbness in skin and vomiting and diarrhea; retention of undigested food; abdominal distension and constipation; and coughing caused by phlegm (See The State Pharmacopoeia Commission of the People's Republic of China, Pharmacopoeia of the People's Republic of China, Chapter I, 204, Chemistry Industry Pressing, Beijing). Also, Magnoliae cortex contains essential oils, such as a, b, g-eudesmol, magnolol, honokiol, tetrahydromagnolol, magnocurarin, obovatol, obovataldehyde, alkaloid, saponin, etc. A characteristic component of Magnoliea cortex was determined to be magnolol (Korea Pharmacopeia, $7^{th}$ revised edition, pp. 782, The Society of Korean Official Compendium of Public Health, Korea Ministry of Health and Welfare).

In studies on the pharmacological effects of Magnoliea cortex, it was demonstrated in in vitro and animal tests that a water extract of Magnoliae cortex has an anti-allergic effect against immediate hypersensitivity reaction (Shin, T.Y., et al., 2001, Arch. Pharm., Res., 24: 249-255). Also, the known pharmacological effects of Magnoliae cortex include apoptotic effects (Park, H. J., et al., 2001, *Arch. Pharm., Res.,* 24: 342-348), NO synthesis-inhibiting effects and TNF-a expression-inhibiting effects (Son, H. J., et al., 2000, *Planata med.,* 66:467-471), antifungal effects (Bang, K. H., et al., 2000, *Arch. Pharm, Res.,* 23: 46-49), mental health-promoting effects (Kuribara, H., et al, 1999, J. Pharm. Pharmacol., 51: 97-103), and skin cancer-inhibiting effects (Komoshima, T. et al., 1991, J. Nat. Prod., 54: 816-822).

Magnolol was demonstrated to have a powerful antioxidive effect (Li, C. et al., 2003, *Bioorganic & Medicinal Chemistry,* 11(17): 3665-3671; Ogata, M., et al., 1997, *J. of the American oil Chemist' Society,* 74(5), 557-562), the effect of preventing hepatocytes from being damaged by D-galactosamine (Park, E. et al., 2003, *Planta Medica,* 69(1): 33-37), an anticoagulation effect (Pyo, M. et al., *Archives of Pharmacal. Research,* 2002, 25(3), 325-328), an antifungal effect (Bang, K. et al., 2000, *Archives of Pharmacal. Research,* 23(1), 46-49), an anxiolytic effect (Maruyama, Y, et al., 1998, *J. Nat. Prod.,* 61(1): 135-138), an acetyl-CoA inhibitory effect (Kwon, B., et al., 1997, *Planta Medica,* 63(6), 550-551), and a cholesterol absorption inhibitory effect (Zhao, C., et al., 1994, *Huazhong Nongye Daxue Xuebao,* 13(4), 373-377). In addition, the present inventors reported that magnolol has the effect of treating diabetic complications (Korean patent application No. 10-2003-39241).

A general method for separating magnolol according to the prior art is as follows.

Magnoliae cortex is extracted by maceration for 24 hours at room temperature, and the extract is filtered. The filtrate is concentrated under reduced pressure to obtain dark-brown methanol extract. The methanol extract is solvent-fractionated with benzene and water to obtain a benzene fraction. The benzene fraction is applied to a silica gel column and eluted with benzene and ethyl acetate (1:0~5:1) to obtain fractions 1, 2 and 3. The fraction is applied to silica gel column and eluted with benzene and ethyl acetate (20:1) to obtain a fraction rich in magnolol. This fraction is applied again to a silica gel column and purified with benzene and ethyl acetate (20:1), thus obtaining a crude crystal. The crude crystal is recrystallized from ethyl acetate to obtain pure magnolol (study on standardization of quality of herbal medicines and materials, Korea Ministry of Health and Welfare, pp. 201-202, 1996).

However, this method has a problem in that it many process steps since after systematic separation, silica gel column chromatography is carried out at least three time to obtain magnolol as a crude crystal, which is then recrystallized.

In addition to this method, reported methods include supercritical fluid $CO_2$ extraction (SFE) (Zhang, Z. et al., Zhongguo yiyuan Yapxue Zazhi, 21(7), 401-402, 2001), capillary electrophoresis (CE) (Zhang, H., et al., 1997, *Analytical Letters,* 30(13), 2327-2339) and the like. However, these methods require expensive equipment and are suitable only for the separation of a small amount of magnolol.

Magnolol separated as described above is a very expensive substance (WAKO no. 137-09081, Catalog 2004, pp. 1196) which is sold at 88,000 Won (Korean currency) per 20 mg by WAKO Co. Ltd., a standard reagent-marketing company in Japan. For this reason, it is uneconomic to use magnolol.

As described above, magnolol shows excellent effects in various views, but is expensive and requires a complicated method and expensive equipment for its separation. For this reason, there is still no report on the mass separation of magnolol. Thus, there is a need for a method allowing magnolol to be separated in large amounts by an economic and simple process.

Accordingly, the present inventors have conducted many studies on a method for separating magnolol, which does not require expensive equipment and at the same time, allows separation process steps to be minimized, thus significantly reducing separation time and cost. As a result, we found that magnolol can be separated from Magnoliae cortex or Magnoliae radix in large amounts, thus completing the present invention.

DISCLOSURE OF INVENTION

Technical Problem

Therefore, it is an object of the present invention to provide a method for the mass separation of magnolol from Magnoliae cortex or Magnoliae radix, which allows a significant reduction in separation process steps, leading to reductions in time and cost.

Technical Solution

The present invention provides a method for the mass separation of magnolol from Magnoliae cortex or Magnoliae radix.

Hereinafter, the present invention will be described in detail.

FIG. 1 is a flow chart showing a method for the mass separation of magnolol from Magnoliae cortex or Magnoliae radix according to the present invention.

As shown in FIG. 1, the inventive method for the separation of magnolol from Magnoliae cortex or Magnoliae radix comprises the steps of: 1) crushing Magnoliae cortex or Magnoliae radix, extracting the crushed material with organic solvent, adding n-hexane to the extract so as to obtain a n-hexane layer; 2) concentrating the n-hexane layer in a water bath at a temperature of 30~40° C. and a revolution speed of 40~200 RPM under reduced pressure so as to obtain a crude crystal; and 3) removing the n-hexane from the crude crystal, completely dissolving the remaining crude crystal in chloroform, adding n-hexane to the solution, and standing the n-hexane-containing solution at room temperature so as to recrystallize the solution.

ADVANTAGEOUS EFFECTS

In the inventive method for the mass separation of magnolol from Magnoliae cortex or Magnoliae radix, a column chromatography step which is necessarily carried out in the general separation process is omitted so that separation process steps are reduced, leading to a saving in separation time. Also, the inventive method does not require expensive equipment, such as a chromatography column, a supercritical extractor or HPLC, and thus, is cost-effective. Accordingly, the inventive method is effective in separating magnolol at low cost.

Also, in the inventive method, the re-crystallization step is repeated so that magnolol with higher purity can be separated.

BRIEF DESCRIPTION OF THE DRAWINGS

FIG. 1 is a flow chart showing a method for the mass separation of magnolol from Magnoliae cortex or Magnoliae radix according to the present invention FIG. 2 shows the results of TLC test of magnolol separated by the inventive method.

BEST MODE FOR CARRYING OUT THE INVENTION

Hereinafter, the method for the mass separation of magnolol from Magnoliae cortex or Magnoliae radix will be described in more detail.

(1) Magnoliae cortex or Magnoliae radix is crushed with a grinder and put in an extraction bag. The plant in the extraction bag is extracted with 80% ethanol in a cold state (4° C.) for about 24 hours. And this extraction procedure was repeated five times.

To extract Magnoliae cortex or Magnoliae radix, it is preferred in the present invention to use the ethanol of water-soluble alcohol as solvent, but if Magnoliae cortex or Magnoliae radix will be obtained, some organic solvent including water-soluble alcohol, can be used.

(2) The extract is filtered and the filtrate is concentrated under reduced pressure until it becomes thick.

(3) To the concentrate, distilled water and n-hexane are added and the n-hexane layer is separated by a separatory funnel.

The n-hexane may be substituted with one among petroleum ether, chloroform and dichloromethane, it is preferred in the present invention to use n-hexane.

(4) The n-hexane layer is concentrated under reduced pressure and when the concentration proceeds to some extent, a crude crystal start to be formed. The concentration is carried out in a water bath at a temperature of about 30~40° C. and a revolution speed of 40~200 RPM. If the concentration temperature is higher than this temperature range or the revolution speed is slower or faster than the speed range, a crystal will not be formed.

(5) As the crude crystal is produced to some extent, the supernatant n-hexane is removed and the crude crystal is completely dissolved in the minimum amount of chloroform. Then, n-hexane is added to the solution and when the solution starts to become hazy, the addition of n-hexane is stopped. Then, the solution is left to stand for 30 minutes at room temperature so that the re-crystallization of the solution occurs.

(6) The supernatant n-hexane is removed, and the remaining crude crystal is dissolved again in the minimum amount of chloroform, and the steps (5) and (6) are repeated until a white crystal is obtained.

The separated crystal was analyzed by TLC and HPLC, and as a result, the crystal was found to be the same compound as magnolol sold by WAKO Co., Ltd, a standard reagent-marketing company in Japan.

In the inventive method for the mass separation of magnolol, a column chromatography step which is necessarily carried out in the general separation process is omitted so that separation process steps are reduced, leading to a saving in separation time. Also, the inventive method does not require expensive equipment, and thus, is cost-effective. Accordingly, the inventive method is effective in separating magnolol in large amounts at low cost.

Mode for the Invention

Hereinafter, the present invention will be described in further detail by examples. It is to be understood, however, that these examples are provided for a better understanding of the present invention and not construed to limit the scope of the present invention.

Example 1

Separation of magnolol from Magnoliae Cortex or Magnoliae Radix

1. Separation of Magnolol from Magnoliae Cortex or Magnoliae Radix 5 kg of Magnoliae cortex or Magnoliae radix was crushed with a grinder and put in an extraction bag. The extraction bag was placed in 10 liter of 80% ethanol, and the crushed plant in the bag was extracted in a cold state (4° C. or room temperature) for about 24 hours. This extraction procedure was repeated five times. The extract was filtered and the filtrate was concentrated under reduced pressure until it became thick. To the concentrate, distilled water and n-hexane were added and the n-hexane layer was separated by a separatory funnel.

The n-hexane layer was concentrated under reduced pressure and when the concentration proceeded to some extent, a crude crystal started to be formed. The concentration was carried out in a water bath at a temperature of about 40° C. and a revolution speed of 100 RPM.

As the crude crystal was formed to some extent, the supernatant n-hexane was removed and the remaining crude was completely dissolved in the minimum amount of chloroform. Then, n-hexane was added to the solution and when the solution started to become hazy, the addition of the n-hexane was stopped. Then, the solution was left to stand at room temperature for 30 minutes so that the re-crystallization of the solution occurred.

Then, the steps of removing the supernatant n-hexane, dissolving the remaining crude crystals in chloroform, slowly adding n-hexane to the solution, and then standing the solution at room temperature so as to form crystals in the solution, were repeated until a pure white crystal was obtained. 60 g (1.2% yield calculated relative to 5 kg of Magnoliae cortex or Magnoliae radix) of magnolol was obtained.

The reason to repeat the steps of removing the supernatant n-hexane, dissolving the remaining crude crystals in chloroform, slowly adding n-hexane to the solution, and then leaving the solution to stand at room temperature so as to form crystals in the solution is that the repeated re-crystallization provides a crystal with higher purity.

In order to examine the purity of the crystal obtained by the repeated re-crystallization step, the crystal before re-crystallization (A) and the crystal after re-crystallization (B) were analyzed by TLC, and the results are shown in FIG. 2. As shown in FIG. 2, the crude crystal (A) contained impurities whereas the recrystallized crystal (B) showed a remarkable reduction in impurities. This indicates that the re-crystallization step provides an increase in the purity of the separated crystal.

2. Structural Analysis of Magnolol

The separated crystal was analyzed by TLC and HPLC, as compared to magnolol sold by WAKO Co. Ltd., a standard reagent-marketing company in Japan, and its molecular weight and molecular formula were determined with a VG high resolution GC/MS spectrometer (Election Ionization MS, Autospec-Ultima). Also, the separated crystal was analyzed by NMR ($^1$H-NMR, DEPT 135, $^{13}$C-NMR, etc), and its molecular structure was determined.

The measurement results are as follows, and the substance separated from Magnoliae cortex or Magnoliae radix in Example was found to be magnolol of the following chemistry figure 1.

Chemistry Figure 1

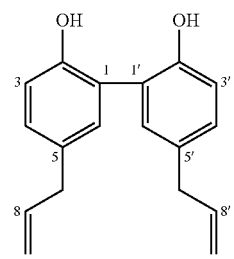

MOLECULAR STRUCTURE OF MAGNOLOL 1) molecular weight: 266
2) molecular formula: $C_{18}H_{18}O_2$
3) $^1$H-NMR (300 MHz, $CDCl_3$): σ (ppm) 3.39 (4H, d, J=6.9 Hz, H-7,7'), 5.12 (4H, m, H-9,9'), 5.86 (2H, d, J=2.4 Hz, OH-2,2'), 6.00 (2H, m, H-8,8'), 6.96 (2H, d, J=8.1 Hz, H-3,3'), 7.12 (2H, d, J=2.4 Hz, H-6,6'), 7.14 (2H, dd, J=8.1, 2.4 Hz, H-4,4')
4) $^{13}$C-NMR (75 MHz, $CDCl_3$): σ (ppm) 39.8 (C-7,7'), 116.3 (C-9,9'), 117.1 (C-3,3'), 124.4 (C-1,1'), 130.3 (C-4,4'), 131.7 (C-6,6'), 133.7 (C-5,5'), 137.9 (C-8,8), 151.4 (C-2,2')

Test Example 1

Test of Production of Magnolol Crystal

In order to establish the conditions for separating magnolol from Magnoliae cortex or Magnoliae radix according to the present invention, the following test was performed while varying only the water bath temperature and the revolution speed.

Example above was repeated while varying only the conditions of the water bath temperature and the revolution speed in concentrating the organic solvent layer under reduced pressure, and whether a crystal has been produced or not was observed.

The results are shown in Table 1.

TABLE 1

| Water bath temperature (° C.) | Revolution speed (RPM) | | | | | | | | |
|---|---|---|---|---|---|---|---|---|---|
| | 20 | 30 | 40 | 80 | 120 | 160 | 200 | 210 | 220 |
| 20 | X | X | X | X | X | X | X | X | X |
| 30 | X | Δ | ○ | ○ | ○ | ○ | ○ | Δ | X |
| 40 | X | Δ | ○ | ○ | ○ | ○ | ○ | Δ | X |
| 50 | X | X | X | X | X | X | X | X | X |

○: production of crystal
Δ: slurry-like state
X: no production of slurry

As shown in Table 1, in the inventive method for the mass production of magnolol from Magnolol cortex and Magnolol radix, the crystal was produced at a water bath temperature of 30~40° C. and a revolution speed of 40~200 RPM. This indicates that these conditions are the optimum conditions to produce the crystal.

INDUSTRIAL APPLICABILITY

Magnolol is known to be able to inhibit the production of advanced glycation endproducts (AGEs) irreversibly produced as a result of the nonenzymatic glycation of protein, which is a typical mechanism causing diabetic complications.

However, magnolol is expensive and thus has limitations in its use. By the inventive method for the mass separation of magnolol from Magnoliae cortex or Magnoliae radix, a separation process of magnolol is shortened and simplified so that magnolol can be separated in large amounts at low cost. Accordingly, magnolol can be widely applied in pharmaceutical compositions and functional food for the prevention and treatment of diabetic complications.

The invention claimed is:

1. A method for a mass separation of magnolol from Magnoliae cortex or Magnoliae radix comprising the steps of:
   1) crushing Magnoliae cortex or Magnoliae radix, extracting the crushed material with organic solvent, adding n-hexane to the extract so as to-obtain a n-hexane layer;
   2) concentrating the n-hexane layer in a water bath at a temperature of 30-40° C. and a revolution speed of 40-200 RPM under reduced pressure so as to form a crude crystal; and
   3) removing the n-hexane from the crude crystal, completely dissolving the crude crystal in chloroform, adding n-hexane to the solution, and leaving the n-hexane-containing solution to stand at room temperature so as to recrystallize the solution, wherein the mass separation does not include a column chromatography step.

2. The method of claim 1, wherein the organic solvent in the step 1) is water-soluble alcohol.

3. The method of claim 1, wherein the n-hexane in the step 1) is substituted with one among petroleum ether, chloroform and dichloromethane.

4. The method of claim 1, wherein the step 3) is repeated in order to obtain a crystal with higher purity.

5. The method of claim 1, wherein said mass separation does not utilize a supercritical extractor or HPLC.

6. A method for the mass separation of magnolol from Magnoliae cortex or Magnoliae radix consisting of:
   1) crushing Magnoliae cortex or Magnoliae radix, extracting the crushed material with organic solvent, adding n-hexane to the extract so as to obtain a n-hexane layer;
   2) concentrating the n-hexane layer in a water bath at a temperature of 30-40° C. and a revolution speed of 40-200 RPM under reduced pressure so as to form a crude crystal; and
   3) removing the n-hexane from the crude crystal, completely dissolving the crude crystal in chloroform, adding n-hexane to the solution, and leaving the n-hexane-containing solution to stand at room temperature so as to recrystallize the solution.

* * * * *